United States Patent [19]

Groitzsch et al.

[11] Patent Number: 4,618,524

[45] Date of Patent: Oct. 21, 1986

[54] MICROPOROUS MULTILAYER NONWOVEN MATERIAL FOR MEDICAL APPLICATIONS

[75] Inventors: Dieter Groitzsch, Hirschberg; Erich Fahrbach, Weinheim, both of Fed. Rep. of Germany

[73] Assignee: Firma Carl Freudenberg, Weinheim, Fed. Rep. of Germany

[21] Appl. No.: 776,811

[22] Filed: Sep. 17, 1985

[30] Foreign Application Priority Data

Oct. 10, 1984 [DE] Fed. Rep. of Germany ....... 3437183

[51] Int. Cl.$^4$ ............................................. B32B 27/14
[52] U.S. Cl. .................................. 428/198; 428/219; 428/284; 428/298; 428/302; 428/903; 428/913
[58] Field of Search ............... 428/198, 903, 248, 302, 428/340, 913, 284, 219

[56] References Cited

U.S. PATENT DOCUMENTS

| 3,879,257 | 4/1975 | Gentile et al. | 428/198 |
| 4,041,203 | 8/1977 | Brock et al. | 428/903 |
| 4,196,245 | 4/1980 | Kitson et al. | 428/198 |
| 4,211,227 | 7/1980 | Anderson et al. | 428/198 |
| 4,287,251 | 9/1981 | King et al. | 428/198 |
| 4,298,649 | 11/1981 | Meitner | 428/198 |
| 4,374,888 | 2/1983 | Bornslaeger | 428/903 |
| 4,436,780 | 3/1984 | Hotchkiss et al. | 428/903 |
| 4,468,428 | 8/1984 | Early et al. | 428/903 |
| 4,493,868 | 1/1985 | Meitner | 428/903 |
| 4,507,351 | 3/1985 | Johnson et al. | 428/198 |

FOREIGN PATENT DOCUMENTS 2132939 7/1984 United Kingdom ............... 428/198

Primary Examiner—James J. Bell
Attorney, Agent, or Firm—Felfe & Lynch

[57] ABSTRACT

A microporous, multilayer material has a layer of microfibers having a weight of from about 0.5 to about 60 g/m$^2$, the microfibers having diameters of from about 0.1 to about 10 microns. The microfiber layer is covered on opposite sides with nonwoven layers and all the layers are bonded together with a pattern of water repellent and, preferably, elastic paste members sufficiently penetrating through the layers. A process for making the microporous, multilayer material imprints the paste for the penetration-bonding paste members on one or both sides of the layers only squeezed dry after washing and water-repellentizing baths.

13 Claims, 5 Drawing Figures

MICROPOROUS MULTILAYER NONWOVEN MATERIAL FOR MEDICAL APPLICATIONS

BACKGROUND OF THE INVENTION

The invention relates to a microporous, multilayer nonwoven material for medical applications such as disposable use in an operating room, for example.

A known, substantially-waterproof, microporous, multilayer nonwoven material is a composite or laminate of a nonwoven layer of hydrophobic microfibers covered on opposite sides by one or more other nonwoven layers. The covering layers may be bonded together by a binding agent, if desired, and all the layers are bonded together into the composite or laminate.

For medical applications such as disposable use in an operating room, the layer of hydrophobic microfibers serves to trap or filter extremely fine particles and bacteria. The covering nonwoven layers serve to prevent the emergence of the microfibers and the matter which they trap or filter out. In this manner, even the escape of bacteria is prevented. It is necessary, however, that the laminate also be substantially waterproof.

For this, water-repellent nonwovens based on polypropylene, for example, or even films are known for the covering layers. All of these materials make the laminate feel unpleasant to wear as a surgical smock, face mask, or other operating-room disposable garment, for example, however, because their very low permeability to air causes the wearer to perspire.

The individual layers of the laminate also are often so poorly bonded together that the laminate has only limited utility for large-area applications such as sheets or surgical drapes. In the case of small pieces, e.g., surgical face masks, the three-layer laminate is held together by stitching or thermal welding, but stitching is too costly for large area disposables and thermal welding presents embrittlement problems.

Although a microfiber layer can be produced in different ways, e.g., by electrostatically spinning a dielectric polymer from a volatile solvent, electrostatic spinning from a fusion, or blowing a molten polymer, electrostatic spinning from a volatile solvent is preferred for augmenting the trap or filter function of the microfiber layer with electrostatic action. It has the disadvantage, however, that only very hard and brittle polymers such as polycarbonate, polysulfone, cellulose triacetate and polystryene or mixtures thereof can be produced by electrostatic spinning from a volatile solvent such as methylene chloride. The strength of such a microfiber layer is very low. It is, therefore, necessary to cover at least one side of such a layer with a tear-resistant supporting material which, as another layer, undesirably adds cost and reduces air permeability.

Moreover, however, when this and/or the other covering layers are thermally welded to such a microfiber layer, very brittle and hard spots are produced which result in an unpleasant feel for a person wearing the material. The embrittlement also creates the danger of cracking or even destroying the microfiber layer with mechanical stress in use. This undesirably reduces the trapping or filtering function of the microfiber layer and encourages penetration and escape of the microfibers through the covering layers. The embrittlement also produces poor draping qualities which make the laminate difficult to use. The welding also destroys most of the additional filtering action desirably achieved in the microfiber layer by electrostatics.

SUMMARY OF THE INVENTION

It is, therefore, an object of the invention to provide a microporous, multilayer nonwoven for medical applications, especially a disposable for an operating-room, which is soft, drapable, and capable of withstanding the mechanical stresses of such use without delamination, cracking or other filter reduction, or the escape of microfibers while being waterproof and breathable, i.e., permeable to air and water vapor, as required for such use.

It is another object of the invention to provide a process for manufacturing the microporous, multilayer nonwoven having the properties specified above.

To these and other ends, a microporous, multilayer nonwoven material has a layer of nonwoven, microfiber material having a weight or density of from about 0.5 to about 60 g/m$^2$, each microfiber thereof being hydrophobic and having a diameter of from about 0.1 to about 10 microns. Nonwoven layers cover opposite sides of the microfiber layer and water-repellent paste members penetrate through the layers in a pattern across the layers sufficiently for bonding the layers together.

The penetration of the paste members through the layers is such that each paste member extends around and about the nonwoven fibers thereof as distinguished, particularly, from a spot-welded, thermally-melted mass of the fiber material. To do this, the paste is preferably imprinted on the multilayered material in the process of making it as later described more fully. The paste may, however, harden into a preferably-elastic solid after imprinting without departing from its definition as a paste, i.e., a bonding material, which, because of its penetration around and about the fibers, however, also does not have to bond to the fibers to bond the layers thereof together, as described.

For the intended medical applications, the covering nonwoven layers are well-draping. For this, they preferably have a weight or density of from about 7 to about 50 g/m$^2$ and preferably, from about 10 to about 40 g/m$^2$. The covering nonwoven layers can be dry-laid or wet-laid materials. Spun nonwoven materials are preferred for heavy use.

It is also desirable that the microfiber layer be spun electrostatically onto one of these layers and then covered with the other. A suitable electrostatic spinning process is described in German Federal Patent Publication No. 20 32 072.

If outstanding drapability is desired, at least one of the covering nonwoven layers can be a light, staple-fiber nonwoven fabric without binding agent. Wear-resistance can be increased by impregnating at least one of the nonwoven covering layers with a binding agent. Both of the covering nonwoven layers are usually made water-repellent, but at least one of the covering nonwoven layers can be partially or wholly made of hydrophilic fibers and, therefore, non-water-repellent. It is, however, much preferred for the nonwoven layers covering the opposite sides of the microfiber layer to be the same.

A water-repellent paste for the water-repellent paste members can be applied to the layers by screen printing to penetrate the entire, triple-layer laminate in the form of rod-like structures. The tops and bottoms of these structures can be shaped as desired. If headed, the paste members then form a type of rivet which makes a particularly-lasting bond. For relatively-thin laminates, imprinting the water-repellent paste on only one covering layer will suffice for sufficient, bonding penetration. For thicker laminates, imprinting the paste on both covering layers such that the paste applied to one reaches that applied to the other at least in places within the laminate is recommended. This can be achieved by a mirror-image, registered imprinting on the opposite covering layers, but can also be achieved, and more easily, by imprinting bilateral patterns, i.e., different or differently-oriented patterns, onto the opposite covering layers such that the patterns intersect. A pattern of narrow bars on one covering layer and a similar pattern on the other oriented so that the bars of the patterns intersect at an angle, and particularly at about 90°, has proven to be especially effective because intersection of these bar patterns is easily assured for contacting the bars with one another in the multilayered material. The resulting structure is, then, rod-like members penetrating through the multilayered material in a pattern, as before, with projections therefrom at opposite ends at the angle at which the bar patterns intersect.

The process for preparing the multilayer nonwoven material first applies the microfiber layer onto a drapable, nonwoven layer, electrostatic spinning having proven especially effective. Then the other, also drapable nonwoven layer is placed thereover. This triple laminate is then preferably lightly pressed together and wound up.

The still-unbound laminate is then washed in water at a temperature preferably above about 60° C. to assure wetting the microfiber layer, squeezed out, and then passed through a bath containing a water-repellentizing agent and again squeezed out. Water-repellent and, preferably, elastic paste is then applied to penetrate the layers to form the paste members bonding the layers together. The material is then dried for use.

Washing the laminate prior to making it water-repellent removes undesired foreign substances, such as those used in preparing for spinning the microfiber layer thereon, and emulsifiers, such as those from a nonwoven covering layer bonded with a binding agent. Also, any foaming adjuvants, wetting agents or the like that may be present are substantially removed.

The washed material is squeezed out to a minimal, residual moisture content before being sent to the repellentizing bath. The residual moisture content, with respect to the dry weight of the laminate, depends on the weight, thickness and structure of the laminate and on the manner in which it was squeezed out, but to assure impregnation with water-repellentizing agent from the bath with the water-repellentizing agent, it is necessary that it be squeezed out more strongly after the washing than after the bath with water-repellentizing agent.

The following mathematical equations apply:

$$n_2 = \frac{G_2(n_1 + 1)}{G_1} - 1;$$

$$g = (n_2 - n_1) \times \frac{F}{100} \times g_{HM} \; n_1 = \frac{N_1}{100}$$

$$g_{FM} = g_{HM} + \Delta G; \; n_2 = \frac{N_2}{100}$$

wherein:
$g_{HM}$ ... Dry weight of unsized half-product in g/m$^2$
$g_{FM}$ ... Dry weight of sized finished material in g/m$^2$
$\Delta g$ ... Weight of the sizing in g/m$^2$ $G_1$ ... Weight of the moist half-product after squeezing out the wash water, in g/m$^2$
$G_2$ ... Weight of the moist half-product after squeezing out the second impregnation (wet-in-wet impregnation)
$n_2$ ... Residual moisture after squeezing out the second impregnation, with respect to the half-product weight $g_{HM}$
$n_1$ ... Residual moisture after squeezing out the wash water, with respect to the half-product weight $g_{HM}$
$N_2$ ... same as $n_2$, but expressed in %
$N_1$ ... same as $n_1$, but expressed in %

From this it is plainly apparent that $n_2$ has to be greater than $n_1$ ($n_2 > n_1$). As a rule, the values of ($n_2 - n_1$) and $n_1$ should be within the following limits:
$n_2 - n_1 \geq 0{,}05$ ($N_2 - N_1 \geq 50\%$)
$n_1 \leq 2.0$ ($N_1 \leq 200\%$)

It is advantageous to keep $n_1$ as low as possible, so as to save energy in the final drying, i.e., to squeeze out the material after washing as heavily as possible without damaging it. Intermediate drying after the washing or repellentizing baths is, however, unnecessary.

The bonding paste is then applied to the material. It was surprising that the bonding paste easily penetrates the extremely-fine microfiber layer and assures a solid bond between the layers by forming rod-like members through the layers. It was moreover surprising that the paste penetrated the microfiber layer while it was still moist with no problem, although the microfiber layer must not be too bulky and heavy for this. This leads to the upper weight limitation of the microfiber layer in the range of from about 0.5 to about 60 g/m$^2$, the lower limit providing filtering density.

The bonding paste preferably is an aqueous dispersion substantially of a polymer of only hydrophobic monomers and no more than about 1.3 wt. % emulsifiers, about 1.0 wt. % low-body, high-molecular-weight thickeners, and about 15 wt. % water-repellentizing agents, the wt. percents being relative to the dry weight of the material dispersed. A paste such as this of very low emulsifier content, no water-soluble agents, or only traces of them, and a water-repellentizing agent, assures perfect penetration of the mircofiber layer for forming the bonding members and prevents leakage of water or degradation of the water-proof quality of the three-layer product.

The paste is best applied through a stencil, the pattern thereof for the bonding members across the layers being generally inconsequential so long as there are sufficient bonding members per unit area in relation to the material of the layers for bonding them together sufficiently for use. If the polymers in the microfiber layer are very brittle, as they are if electrostatically spun from a solution, for example, it is desirable for the spacing of the preferably-elastic, paste bonding members to be close.

Bonding the three layers together with the pattern of paste members makes the layered material resistant to tearing as well as separation. It also provides flexibility, even when very hard and brittle polymer materials compose the microfiber layer. Selection of the microfiber material, the bonding paste and the water-repellentizing agents in the bonding paste and material-impregnating both adapts the multilayer nonwoven to the requirements for use.

In addition to disposable products, it is, therefore, also possible to manufacture reusable products. To enable reusable products to withstand washing and cleaning, however, it is important to use wettable repellentizing agents and binding agents. Such agents and their corresponding properties are known and obtainable commercially.

When bulky and heavier materials are to be spot-bonded with the bonding paste, it is desirable to add an effective antifoaming agent, on a silicone basis, for example, to the water-repellentizing agent for impregnating the material in the bath. The bonding paste is then used in a foamed form. The effective antifoaming agent is one by which contact of the foamed paste and still-wet composite nonwoven containing the antifoaming agent will cause a spontaneous collapse of the bonding-paste foam, combined with a great reduction of the viscosity of the bonding paste, during the stenciling or other process by which paste is applied for penetrating the material. This facilitates the penetration of even relatively-thick and bulky composite nonwovens.

The draping qualities of the nonwoven materials used for the covering layers can be improved by a mechanical softening process. This is especially advantageous when the covering nonwovens are wet-laid.

The water-repellent bonding paste and the water-repellentizing agent impregnated into the material materially aid waterproofing the material. The difference between a 3-ply laminate impregnated with water-repellentizing agent and one that is not is all the greater as the weight ratio between the covering nonwovens and the hydrophobic microfiber layer increases.

To increase the moisture-absorbing capacity of the material, if desired, however, at least one of the laminates, and generally one of the covering layers, can contain absorbent fibers, cotton or cellulosic, for example, partially or fully. The full absorbency of such fibers is usually achieved after washing. This layer then should be only spot bonded pattern wise with a binding agent, if desired, but if swelling binding agents are used, i.e., those which are absorbent, not on the basis of surfactants (tensides), but on the basis of their polymeric structure and low degree of crosslinking, full-surface bonding of the nonwovens is also possible because the washing which removes the water-soluble components does not, in this case, result in a loss of absorbency. Such nonwovens, due to their high absorbency and their uncrimped structure, are relatively flat. They can be, therefore, easily penetrated by the bonding paste. Such nonwovens, due to their breatheability, are also pleasant to wear and are, therefore, always preferred when great wearing comfort is desired.

Although the microfiber layer can have a thickness for a weight or density from about 0.5 to about 60 g/m$^2$ with fibers of from about 0.1 to about 10 microns, depositing the fibers by electrostatic spinning from solution can achieve weights of less than 1 g/m$^2$ with an extremely uniform distribution. The preferred weight range of the microfiber layer is, as a rule, between 1 and 30 g/m$^2$.

The deposit of the microfibers will depend on the requirements for resistance to the penetration of water, filtration effect for bacteria, etc., and water vapor permeability. For waterproofing of 40 mbar, measured by German Industrial Standard (DIN) Standard 53 886/77, for example, a microfiber deposit of 8 g/m$^2$ will suffice, the microfibers being composed of 93 wt.-% of polycarbonate and 7 wt.-% of polystyrene, laid by electrostatic spinning out of a solution with a fineness of 4.5 microns when the microfiber layer is covered on both sides with a wet-laid nonwoven containing cellulose/cotton and weighing 20 g/m$^2$, as later described (Example 2).

DESCRIPTION OF THE DRAWINGS

Merely exemplary embodiments of materials and processes of their manufacture illustrate but do not limit the invention and are shown in drawings, in which.

DESCRIPTION OF THE PREFERRED EMBODIMENTS OF MATERIALS AND PROCESSES

Figure 1:
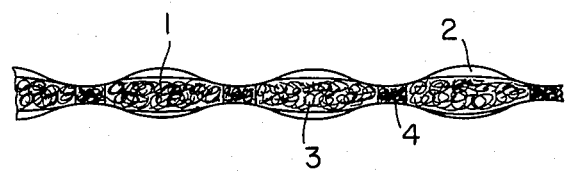
FIG. 1 is an elevation of one material.
Figure 2:
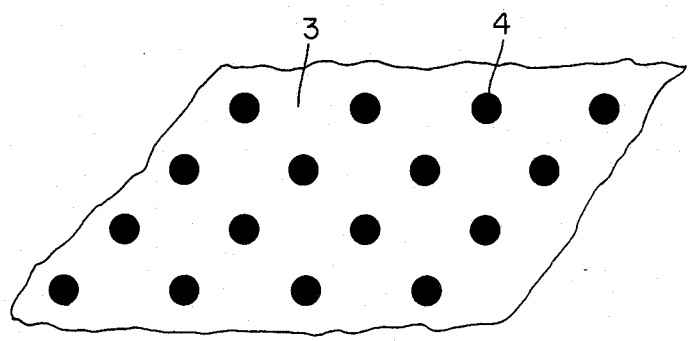
FIG. 2 is a plan view of the material of FIG. 1.

FIGS. 1 and 2 show a three-ply microporous nonwoven material. A nonwoven layer 1 of hydrophobic, dielectric microfibers is between nonwoven covering layers 2, 3. Either or both covering layers 2, 3 may also be water repellent in dependence on fiber content and treatment as described above. Rod-like, elastic, water-repellent paste members 4 penetrate the layers in a pattern across the layers to spot bond them together permanently. The regular pattern of the paste members across the layers is best seen in FIG. 2.

Figure 3:
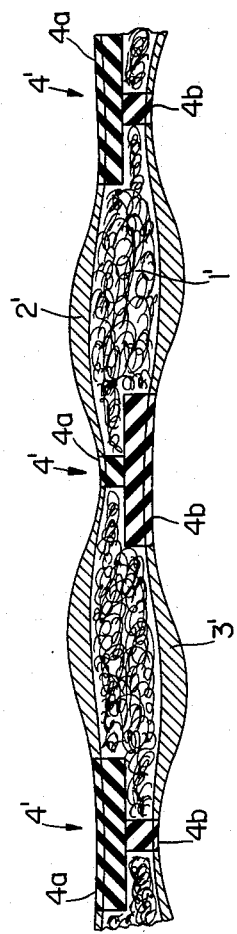
FIG. 3 is a sectional elevation of another material.

FIG. 3 shows a material similar to that of FIGS. 1 and 2, except that the rod-like elastic, water-repellent, paste, layer-bonding members at 4 are, in this case, formed by the contacting portions of upper and lower bars 4a,4b, each penetrating only part way through the multilayered, microporous material in a registered pattern of alternately oriented bars across the layers defining an angle, here 90°, between the intersections of the bars. The result is projections along the material from opposite ends of the rod-like members at 4 penetrating the material.

Figure 4:
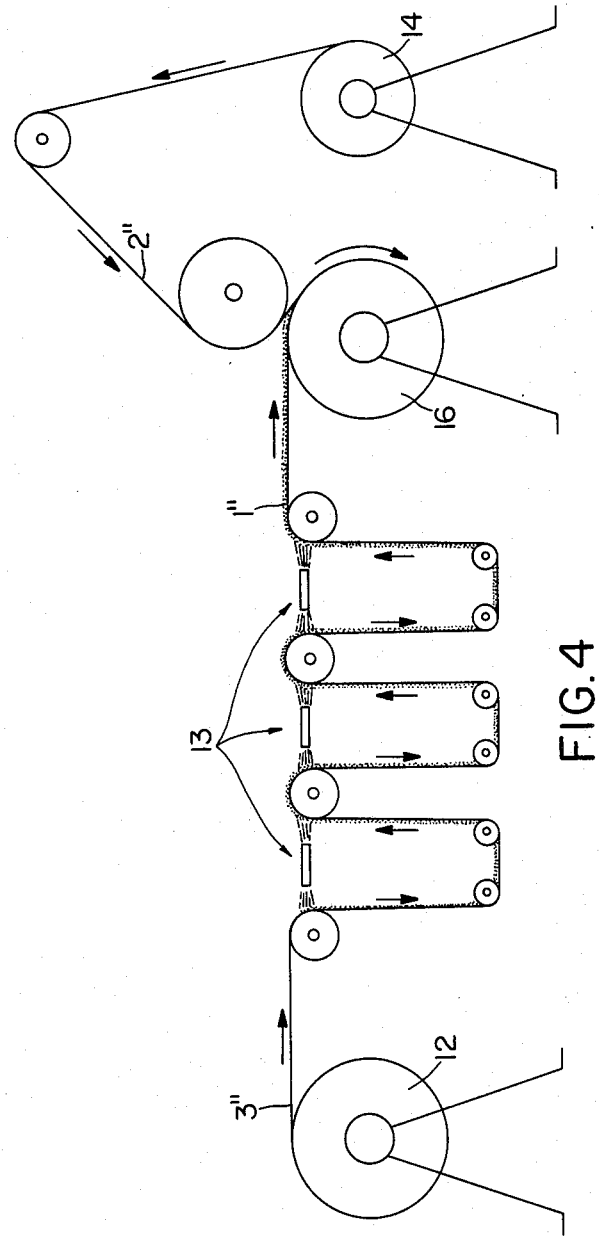
FIG. 4 is a schematic of a first portion of a process for making a material.
Figure 5:
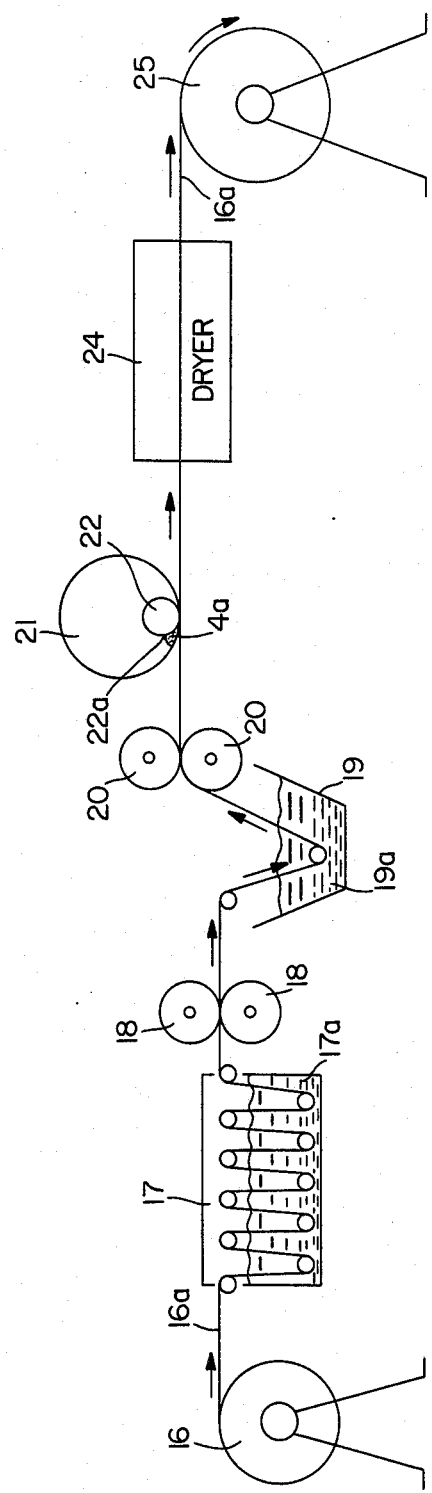
FIG. 5 is a schematic of the remaining portion of the process for making the material of FIG. 4.

FIG. 4 diagrams a first portion of a manufacturing process for producing a three-ply, microporous nonwoven material. In it, a first layer of appropriate nonwoven material 3″ for one side of the three-ply material is pulled from a roll 12 thereof and fed through a three-stage electrostatic spinning system at 13. The spinning system electrostatically deposits an appropriate, microfiber layer 1″ on one side of the nonwoven layer 3″ as the nonwoven layer 3″ passes successively through the three stages of the spinning system at 13. A second layer of appropriate nonwoven material 2″ is then fed from a roll 14 thereof and loosely joined to the other layers by lightly pressing and/or tensioning it against the microfiber layer 1″ as a covering layer thereover as all three layers are wound on a roll 16 thereof. Appropriate materials and dimensions for the three plys are, of course, those previously described and hereafter described by way of Examples.

The roll 16 of the three, loosely-joined plys is then transferred to the second portion of the manufacturing process diagrammed in FIG. 6. Here, the three plys 16a are unwound and fed through a washing machine at 17. The washing machine holds washing liquid 17a at a temperature above 60° C. to assure liquid penetration of the three plys for washing them.

The washed plys are then passed between wringer rollers 18 to squeeze out the washing liquid to the degree previously described. From the wringer rollers 18, the plys are passed through a bath of liquid 19a in a tub 19. The liquid 9a contains the agent for water repellentizing the plys as previously and hereafter described.

After impregnation with the water-repellentizing agent from liquid 19a, the plys 16a are passed between further wringer rollers 20. As previously described, the wringer rollers 20 squeeze liquid out of the plys in relation to that of prior wringer rollers 18 and, preferably, substantially to minimize the requirements for a dryer 24 through which the plys will pass later in the process.

The plys 16a then pass cooperative supply and imprinting rolls 21,22 which supply and imprint a water-repellent, elastic paste 4a onto one side of the plys appropriately for the paste 4'' to penetrate all three plys. The imprinting roll 22 has a surface feature 22a such that the imprinting with the binding paste is in a pattern along the plys progressing thereby in a known way and as previously described.

The plys 16a are, therefore, now bound together by the pattern of elastic, water-repellent paste members (e.g., 4 in FIG. 1) which penetrate through the plys in the pattern thereacross determined by the imprinting roll 22. The now-bound plys are, therefore, now passed through a dryer 24 for drying and wound on a roll 25 to be ready for use such as making it into disposable garments for an operating room.

The materials and processes of their manufacture are further illustrated by the following specific Examples.

EXAMPLE 1

(Blank test to demonstrate the state of the art)

On a wet nonwoven having a weight of 20 g/m$^2$, consisting of 70% of unground cellulose and 30% of cotton of dt 1.7/5 mm, bonded with a water-repellent, low-emulsifier polyacrylic acid ester dispersion of medium-soft film hardness (T300=approx. −14° C.; T300 is the temperature at which the torsion modulus of an air-dried film has a value of 300 kg/cm$^2$) and having a binding agent content of 30% with respect to the nonwoven weight, microfibers of 93% polycarbonate and 7% polystyrene were deposited by electrostatic spinning from methylene chloride solution.

The microfiber deposit amounted to 8 g/m$^2$. The fiber fineness varied between 1.9 and 9.4 microns, averaging 4.5 microns in 20 fibers.

After spinning, the second side of the microfiber layer was covered with the same wet nonwoven of 20 g/m$^2$, lightly pressed, and wound up.

The waterproof rating, determined according to DIN 53 886/77, of the loose 3-ply laminate, amounted to 20 mbar. The bond strength of the three layers to one another was virtually 0, as it appears from the following test report.

Maximum traction force, longitudinal 33 N/5 cm; elongation at MTF, longitudinal: 7%
Maximum traction force, transverse 14 N/5 cm; elongation at MTF, transverse: 14%
Separating strength: 0.4 N*
Permeability to air: 140 l/sec/m$^2$ at 0.5 mbar
Thickness: 0.60 mm

* The separation takes place within the micro layer. The layers shift on one another when lightly pressed with the hand.

Such a material can be used only in making small articles, such as disposable surgical masks, especially on account of the poor bond strength. For large-surface applications, such as protective garments or operating room covers, goods made in accordance with Example 1 are too stiff, too hard, drape too poorly, and are much too weak in their laminate bond.

EXAMPLE 2

The 48 g/m$^2$ laminate with the central microfiber layer prepared in Example 1 is represented diagrammatically in FIG. 2 . In a drum-type washing machine it is continuously washed first at 60° C. and then at room temperature, and squeezed as dry as possible in a wringer. Then it is passed through an aqueous bath consisting of an 8% mixture of water-repellentizing agent, i.e., the above-described wet-in-wet impregnation is performed.

The amount absorbed, reckoned with respect to air-dried nonwoven, amounted to 35% (=1.34 g solid per m$^2$). The water-repellentizing agent was an emulsion of paraffin containing zirconium salt. Immediately after the water-repellentizing agent was squeezed out, the moist material was stenciled on one side with a foam bonding paste by means of a 10-mesh round screen stencil, with the aid of a magnetic pressure squeegee.

Formula of the mixture: (solid content 40%)

|  | Parts solid | Parts liquid |
| --- | --- | --- |
| Water | — | 16.0 |
| Anionic foaming agent | 0.8 | 4.0 |
| Green pigment preparation | 0.5 | 1.0 |
| Weakly cationic water-repellentizing agent (40%) | 12.0 | 30.0 |
| 3% methylcellulose original mixture | 0.3 | 10.0 |
| Water-repellent polyacrylate dispersion of very low emulsifier content | 100.0 | 222.0 |
| Total | 113.2 | 283.0 |

The methylcellulose had an average degree of substitution of 1.4 to 1.6 and a Hoeppler viscosity in 2% solution of 20,000 CP. The bonding paste was applied in an amount of 10 g/m$^2$ of solid substance. The viscosity of the unfoamed mixture was 995 CP Brookfield, measured with a No. 4 spindle at 20 rpm. The mixture was foamed to a liter weight of 200 g (pot weight 200 g/liter).

After drying, the material was relatively stiff and therefore was made soft and drapable mechanically by crumpling with the hand.

The following measurements were made:

| | |
| --- | --- |
| Total weight | 53 g/m$^2$ |
| Maximum traction force, longitudinal: | 37 N/5 cm, |
| elongation at MTF, longitudinal: | 14% |
| Maximum traction force, transverse: | 20 N/5 cm, |
| elongation at MTF, transverse: | 20% |
| Thickness: | 0.44 mm |
| Permeability to air: | 120 l/s/m$^2$ at 0.5 mbar |
| Resistance to separation: | 1.6 N* |

*Shifting of the layers on one another is absolutely impossible.

It is amazing to what extent it is possible in Example 2 to increase the waterproof quality and, in part, the elongation and resistance to separation, above those of the blank test 1. In conjunction with this very high waterproofing, Example 2 has an extremely high permeability to air. On the basis of this fact, a material made in accordance with Example 2 could be used as an operating-room cover cloth.

We know of no method whereby, at such a low weight of 58 g/m$^2$, such an enormously high waterproofing can be combined with such a high permeability to air. Water-repellent, nonwoven, disposable operating-room cover cloths with water-repellancies of 17 to 23 mbar, and at weights of 62 to 80 g/m², have, depending on the way they are manufactured and their weight, air permeabilities of approximately 30 to 250 l/s/m² at 0.5 mbar of air pressure.

EXAMPLE 3

Preparation of the green supporting material for covering with microfibers

On a transversely laid sliver of 7 g/m² of a mixture of polyester fibers of dtex 1.7/38 mm and cotton of dtex 1.3/40 mm=70×30, there is laid a longitudinal sliver weighing 7 g/m² composed of 100% cotton. The 2-layer fiber sandwich is bonded by means of impregnation with foam bonding agent. The plastic dispersion consists of 70 parts solid of a soft, self-crosslinking polyacrylate (Acronal 35 D) and 30 parts solid of an adhesive raw material (Acronal 80 D).

An anionic foaming agent, a wetting agent on a basis of sulfosuccinate, and a green pigment are added to the impregnant mixture. The ratio of fiber material to bonding agent amounted to 74:26, and the weight of the supporting nonwoven was 19 g/m². The nonwoven had a highly absorbent character. The supporting nonwoven was covered electrostatically with the polymer solution of Example 1, except that this time the average fiber fineness of the microfibers was 2.8 microns (scatter of 1.1 to 7.8 microns).

The microfiber coating amounted to 8 g/m². A polyamide spun nonwoven fabric with a fine fiber titer (approx. 2.0 dtex), weighing 10 g/m² and spot-welded (24% welded area), was laid onto the uncovered microfiber layer and lightly pressed. Then, as described in Example 1, the material was washed, wet-in-wet water-repellentized, wet-in-wet stenciled with a foam paste containing water-repellentizing agent, and dried. The amount of water-repellentizing agent applied was 0.8 g/m² and the amount of foam paste was 7 g/m², so that a finished material weight of 44.8 g/m² resulted.

The strong wetting properties of the supporting nonwoven fabric promote the thorough wetting of the microfiber layer in the washing process.

The following values were determined:

| | |
|---|---|
| Waterproof rating: | 57 mbar |
| Permeability to air: | 45 l/s/m² at 0.5 mbar |
| Water-vapor permeability: | 26 mg cm²/h |
| Maximum traction force, longitudinal: | 116 N/5 cm |
| Maximum traction force, transverse: | 52 N/5 cm |
| Continued tearing force, longitudinal: | 6.4 N/5 cm |
| Continued tearing force, transverse: | 8.3 N/5 cm |

The waterproof rating is so high that it is not possible, even with high mechanical stress (such as striking the fist against a puddle of water spread out over the material) to make the water pass through. The water-vapor permeability, on the other hand, is very high. For this reason, a water-repellent material prepared in accordance with Example 3 could be used as a draping, semi-permeable laminate with a microporous microfiber core, in the making of raincoats. The breathability and the high water-vapor permeability provide for pleasant wearing qualities without the danger of internal sweating.

EXAMPLE 4

This example differs from Example 3 only in that the microfiber layer of 8 g/m² was reduced to 2.5 g/m².

The weight of the finished material was only 39 g/m². The following ratings were determined:

| | |
|---|---|
| Waterproof rating: | 24 mbar |
| Permeability to air: | 182 l/s/m² at 0.5 mbar |
| Maximum traction force, longitudinal: | 98 N/5 cm |
| Maximum traction force, transverse: | 48 N/5 cm |
| Continued tearing force, longitudinal: | 6.0 N |
| Continued tearing force, transverse: | 8.5 N |
| Draping coefficient: | 44%. |

The goods produced in accordance with Example 4 have a very high waterproof characteristic for their very light weight. The drapability (draping coefficient) is very good and is favored by the low weight. The material can be used as a disposable operating-room smock material. By methods of the state of the art, nonwoven fabric weights of at least 71 g/m² are necessary for the same application. The saving in weight and hence the saving in raw material is therefore considerable.

It will be understood that the specification and examples are illustrative but not limitative of the present invention and that other embodiments within the spirit and scope of the invention will suggest themselves to those skilled in the art.

What is claimed is:

1. A microporous, multilayer nonwoven material, comprising:
   a layer of nonwoven, microfiber material having a weight of from about 0.5 to about 60 g/m², each microfiber thereof being hydrophobic and having a diameter of from about 0.1 to about 10 microns;
   nonwoven layers covering opposite sides of the microfiber layer; and
   water-repellent paste members penetrating through the layers in a pattern across the layers sufficient for bonding the layers together.

2. The material of claim 1, wherein the paste members are elastic and rod-like.

3. The material of claim 2, wherein each rod-like paste member has at lest one projection from each end along the layers, whereby the paste members may have been imprinted as bars onto opposite sides of the material with each bar penetrating into the material only far enough for contacting the bar from the other side.

4. The material of claim 3, wherein the projections from each end of the paste members are at an angle of about 90° to each other, whereby the bars were similarly oriented when imprinted.

5. The material of claim 1, wherein at least one of the covering nonwoven layers contains a water-repellent agent.

6. The material of claim 2, wherein at least one of the covering nonwoven layers contains a water-repellent agent.

7. The material of claim 3, wherein at least one of the covering nonwoven layers contains a water-repellent agent.

8. The material of claim 1, wherein at least one of the covering nonwoven layers contains hydrophilic fibers.

9. The material of claim 2, wherein at least one of the covering nonwoven layers contains hydrophilic fibers.

10. The material of claim 3, wherein at least one of the covering nonwoven layers contains hydrophilic fibers.

11. The material of claim 5, wherein at least one of the covering nonwoven layers contains hydrophilic fibers.

12. The material of claim 1, wherein at least one of the covering layers has a pattern-wise bonding agent therein.

13. The material of claim 2, wherein at least one of the covering layers is full surface bonded with a swellable bonding agent.

* * * * *